(12) United States Patent
Moszner et al.

(10) Patent No.: US 6,172,131 B1
(45) Date of Patent: Jan. 9, 2001

(54) HYDROLYSIS-STABLE AND POLYMERIZABLE ACRYLPHOSPHONIC ACIDS

(75) Inventors: Norbert Moszner, Eschen; Frank Zeuner; Volker Rheinberger, both of Vaduz, all of (LI)

(73) Assignee: Ivoclar AG, Liechtenstein ( * ) Notice: Under 35 U.S.C. 154(b), the term of this patent shall be extended for 0 days.

(21) Appl. No.: 09/169,066

(22) Filed: Oct. 9, 1998

Related U.S. Application Data
(60) Provisional application No. 60/071,496, filed on Jan. 14, 1998.

(30) Foreign Application Priority Data

Oct. 16, 1997 (DE) ............................................. 197 46 708

(51) Int. Cl.⁷ ............................ A61K 6/083; C07C 69/54
(52) U.S. Cl. .......................... 523/116; 523/118; 524/547; 526/278; 562/8; 562/20; 562/598
(58) Field of Search .................................... 523/116, 118; 526/278; 524/547; 562/8, 20, 598

(56) References Cited

FOREIGN PATENT DOCUMENTS 0 431 740  6/1991  (EP) .
2 089 807  6/1982  (GB) .

OTHER PUBLICATIONS

Ikemura et al., "Preparation of Carboxyalkylphosphonic Acid and (Meth)acrylic Diesters as Adhesive Compositions," *Chemical Abstracts* 117(9) (1992).
Kawamoto et al., "Novel Class of Difluorovinylphosphonate Analogs of PEP," *J. Chem. Soc.*, 97(8):1249–1253 (1997).

*Primary Examiner*—Andrew E. C. Merriam
(74) *Attorney, Agent, or Firm*—Nixon Peabody LLP

(57) ABSTRACT

Hydrolysis-stable and polymerizable acrylphosphonic acids are described which are particularly suitable as a component of dental adhesives owing to their adhesion-promoting properties.

9 Claims, No Drawings

HYDROLYSIS-STABLE AND POLYMERIZABLE ACRYLPHOSPHONIC ACIDS

This applicable claims priority benefit of U.S. patent application Ser. No. 60/071,496, filed on Jan. 14, 1998, which is hereby incorporated by reference.

The present invention relates to polymerizable acrylphosphonic acids which have a high degree of hydrolytic stability and are suitable in particular for the preparation or as components of polymers, adhesives or other materials and in particular of dental materials.

Polymerizable phosphonic acids are of importance in polymer chemistry above all as comonomers, and they allow the preparation of organic polymers in which thermal stability, adhesive properties, flammability and solubility in polar solvents are improved. To this end, numerous monomeric phosphonic acids having polymerizable vinyl, dienyl, allyl or styryl groups were synthesized and polymerized. An overview of phosphonic acids is given by Houben-Weyl, Methoden der Organischen Chemie, Volume E 20, (2nd part), Georg Thieme Verlag, Stuttgart-New York 1987, page 1300 et seq. Examples of such conventional polymerizable phosphonic acids are vinylphosphonic acid, allylbenzenephosphonic acid, α-aminoallylphosphonic acid, phenylethenephosphonic acid, 1,3-butadiene- or isoprenephosphonic acid, 4-vinylbenzenephosphonic acid or 2-(4-vinylphenyl)-ethane phosphonic acid.

However, phosphonic acids in which the double bond is bound to the phosphorus atom directly or via an oxygen atom, such as vinylphosphonic acid or ethylphosphonic acid monovinyl ester, exhibit an only moderate tendency to homopolymerization. Therefore, only homopolymers with a small molecular weight can be obtained from them. In contrast, high-molecular-weight polymerizates can be obtained from (meth)acrylphosphonic acids or esters in which the (meth)acrylic group is not bound directly to the phosphorus. Known (meth)acrylphosphonic acid derivatives are e.g. the phenylphosphonic acid-mono-(methacryloyloxyethyl)-esters of formula (a) or tert-butylphosphonic acid mono[1,3-di(methacryloyloxy)propan-2-yl]-esters of formula (b), described in DE-B-27 11 234.

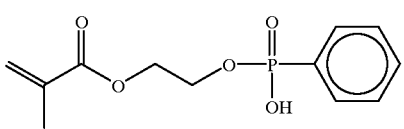

(a)

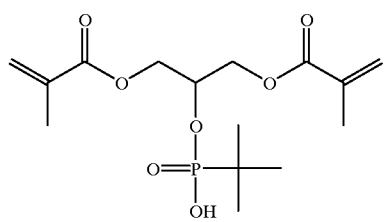

(b)

Moreover, acrylic acid-(2-phosphono-1,1-dimethylethylamine) is known from DE-A-32 10 775 and methacrylic acid-(2-phosphono-1,1-dimethylethylamine) of the formula (c) is known from DE-A-33 13 819 and JP 62-63314 (Chem. Abstr. 107 (1987), 41318f).

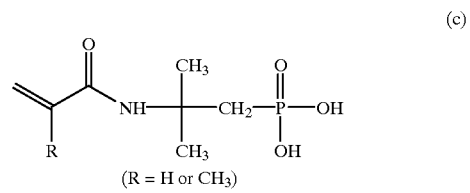

(c)

(R = H or CH$_3$)

Acrylic acid-(2-phosphono-1,1-dimethylethylamine), also called acrylamido-2-methylpropanephosphonic acid, is used in the form of its homo- or copolymers as corrosion inhibitors (cf. EP-B-89 654 and U.S. Pat. No. 4,650,591).

Finally, N-acryl-aminomethanebisphosphonic acid of the formula (d) is also described in DD-A-273 846.

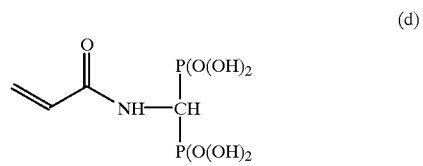

(d)

All of these known (meth)acrylphosphonic acid derivatives are, however, not stable in aqueous solution. Rather, a hydrolytic cleavage of the (meth)acrylic group takes place which is even catalysed by dissociated protons of the phosphonic acid group and thereby accelerated.

However, the use of aqueous solutions is advantageous or absolutely necessary in a whole series of applications of polymerizable phosphonic acids. This is e.g. the case in the preparation of low-viscosity adhesives which are free of organic solvents, or in that of dental adhesives which result in an optimum wetting of the moist dentine surface only in aqueous form.

It is therefore the object of the invention to make available polymerizable acrylphosphonic acids which are hydrolysis-stable in aqueous solution and have good adhesion properties, can be polymerized using conventional radical initiators and are therefore suitable as a component of in particular adhesives, shaped bodies, cements or composites and above all of dental materials.

This object is surprisingly achieved by the hydrolysis-stable and polymerizable acrylphosphonic acids according to claims 1 and 2.

The subject of the present invention is also the process for the preparation of the acrylphosphonic acids according to claim 3, the use thereof according to claims 4 to 6, the dental material according to claims 7 and 8, and polymers and copolymers of the acrylphosphonic acids according to claim 9.

The acrylphosphonic acids according to the invention are compounds of the following general formula (I), stereoisomers thereof and mixtures of such stereoisomers

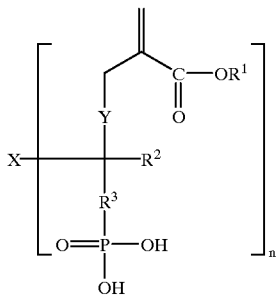

(I)

where $R^1$, $R^2$, $R^3$, X, Y and n, unless stated otherwise, independently of one another have the following meanings:

$R^1$=hydrogen, $C_1$ to $C_{10}$ alkyl or $C_6$ to $C_{10}$ aryl,

R=hydrogen, fluorine, $C_1$ to $C_5$ alkyl or phenyl, $R^3$=$C_1$ to $C_8$ alkylene, phenylene or is absent, Y=oxygen, sulphur, $C_1$ to $C_8$ alkylene or is absent, n=1 or 2, and with the proviso that (a) for n=1

X=hydrogen, fluorine, $C_1$ to $C_5$ alkyl or $C_6$ to $C_{12}$ aryl, and (b) for n=2

X=$C_1$ to $C_{10}$ alkylene, $C_6$ to $C_{10}$ arylene, $C_7$ to $C_{20}$ arylenalkylene or is absent.

The individual alkyl and alkylene radicals can be straight-chain, branched or cyclic. Moreover, the individual alkyl, aryl, alkylene, arylene, phenyl, phenylene and arylenalkylene radicals can bear one or more substituents, such as Cl, Br, $CH_3$, $C_2H_5$, $CH_3O$, OH, COOH, CN or $NO_2$.

There also exist for the above-mentioned variables of the formula (I) preferred definitions which, unless otherwise stated, can be chosen independently of one another and are as follows:

$R^1$=hydrogen, $C_1$ to $C_5$ alkyl or phenyl, $R_2$=hydrogen, fluorine or $C_1$ to $C_3$ alkyl, $R^3$=$C_1$ to $C_3$ alkylene, phenylene or is absent, Y=oxygen, $C_1$ to $C_3$ alkylene or is absent, n=1 or 2, and with the proviso that (a) for n=1

X=hydrogen, fluorine, $C_1$ to $C_3$ alkyl or phenyl, and (b) for n=2

X=$C_1$ to $C_6$ alkylene, phenylene or is absent.

Preferred compounds are therefore those in which at least one of the variables of the formula (I) has the above-described preferred definition, the formula (I) including all stereoisomers made possible by the mentioned substituents and their mixtures, such as racemates.

The acrylphosphonic acids according to the invention of the formula (I) can be prepared by reaction of α-halomethylacrylic acid esters of the formula (II) with protected mono- or difunctional phosphonic acid esters of the formula (III) and cleavage of the protective groups. In the formulae (II) and (III) U is halogen, SG is protective group and the other variables are as defined above for formula (I). This reaction can be illustrated by the following general reaction equation which is followed by a concrete example.

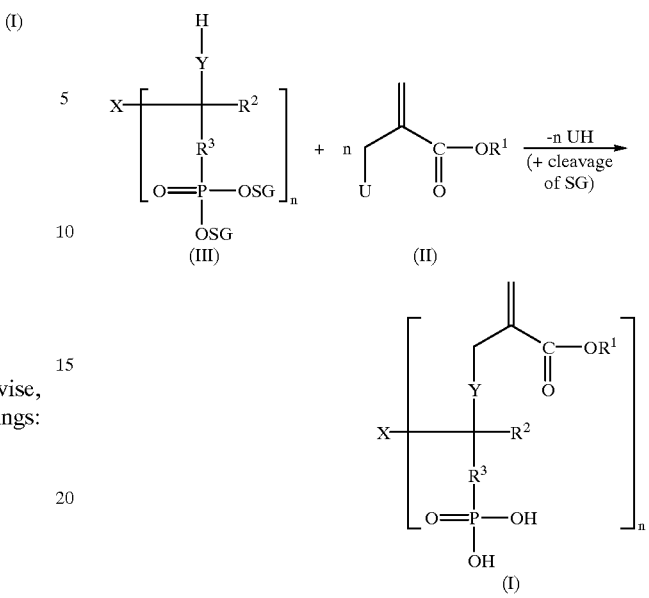

Concrete example:

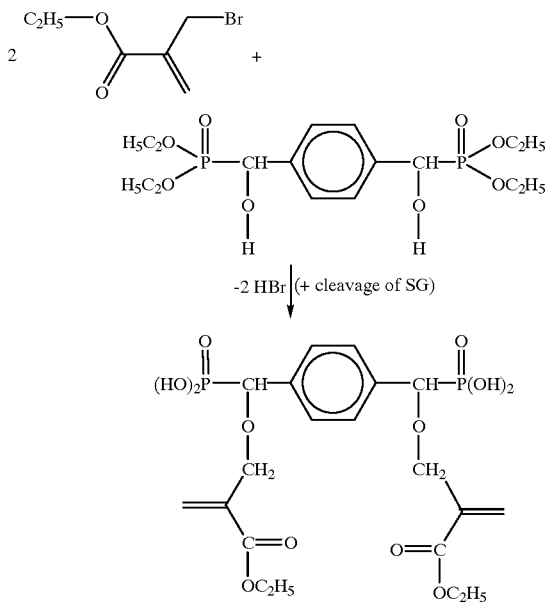

The reaction can be conducted by using the methods known from organic chemistry for forming C—C, C—O or C—S bonds (cf. C. Weygand, G. Hilgetag, Organisch-chemische Experimentierkunst, Johann Ambrosius Bart Verlag, Leipzig 1970, pages 963 et seq., 362 et seq. and 657 et seq.).

Used as protective groups (SG) are customary protective groups for phosphoric acid groups, such as ester groups, in particular SG is ethyl. After the reaction has taken place, these are split off according to conventional processes, in order to liberate the acrylphosphonic acids of the formula (I). The hydrolytic cleavage of the protective groups SG is effected in particular by silylation with trialkylsilanes, e.g. trimethylsilyl chloride mixed with sodium iodide or bromide, and subsequent reaction with alcohols or water (cf. S. Freeman, J. Chem. Soc., Perkin Trans, 2 (1991) 263).

The α-halomethylacrylic acid esters (II) used as starting materials can be obtained e.g. by reaction of the corresponding acrylic acid esters with formaldehyde in the presence of 1,4-diazabicyclo[2,2,2]octane (DABCO) and subsequent halogenation with inorganic acid chlorides, such as $SOCl_2$, $PCl_3$ or $PBr_3$ (cf. L. J. Mathias et al., Macromolecules 20 (1987) 2039, 2326, J. Polym. Sci.: Part A: Polym. Chem. 32 (1994) 2937), and this reaction is illustrated by the following equation and a concrete example:

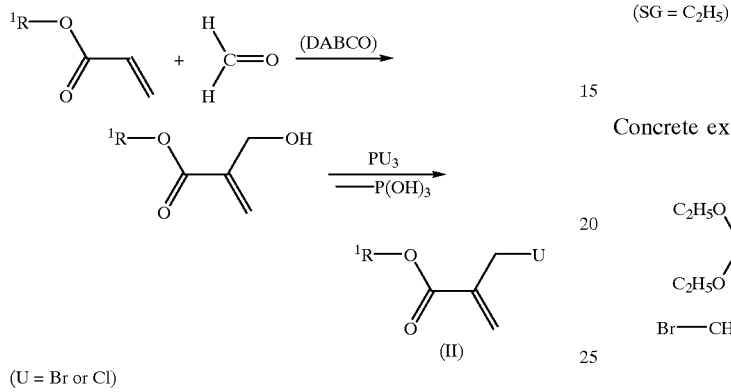

(U = Br or Cl)

Concrete example:

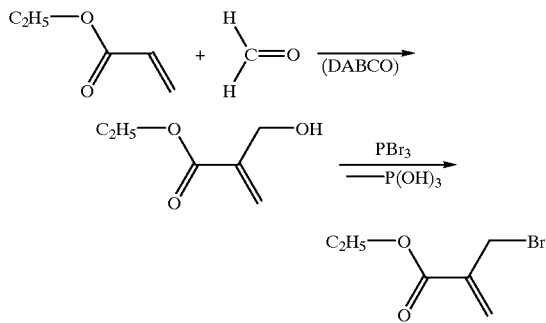

Suitable protected mono- or difunctional phosphonic acid esters (III) can be obtained by different methods. A particularly suitable method proceeds via the Michaelis-Arbusow reaction for the preparation of alkylphosphonic acid esters (cf. G. M. Kosolapoff, Org. Reactions 6 (1951) 273). In this process, trialkyl phosphites, e.g. triethyl phosphite, and haloalkanes are reacted in accordance with the equations below, in which the Y—H group must also be protected where necessary.

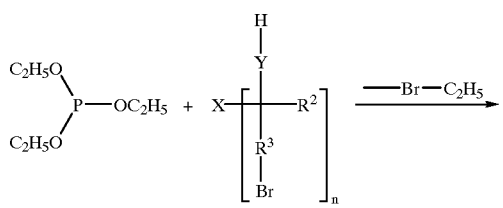

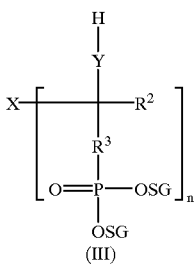

(SG = $C_2H_5$)

Concrete example:

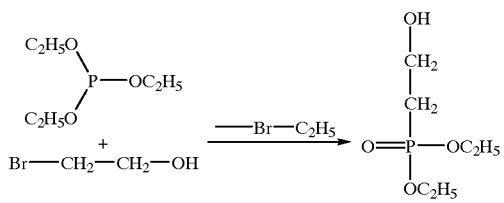

Arylphosphonic acids can be obtained e.g. by Friedel-Crafts reaction of aromatic hydrocarbons with phosphorus trichloride in the presence of aluminium trichloride, chlorination of the formed dichlorophosphine to tetrachlorophosphine and subsequent hydrolysis to the phosphonic acid (cf. G. M. Kosolapoff, Org. Reactions 6 (1951) 273).

Furthermore, protected hydroxyalkylphosphonic acid esters (Y—H≡OH) where $R^3$=absent can be prepared by adding dialkyl phosphites with base catalysis to mono- or difunctional aldehydes or ketones analogously to the process according to F. Texier-Boullet, A. Foucaud, Synthesis, 1982, 916. This type of reaction and a concrete example thereof are shown by the following reaction equations:

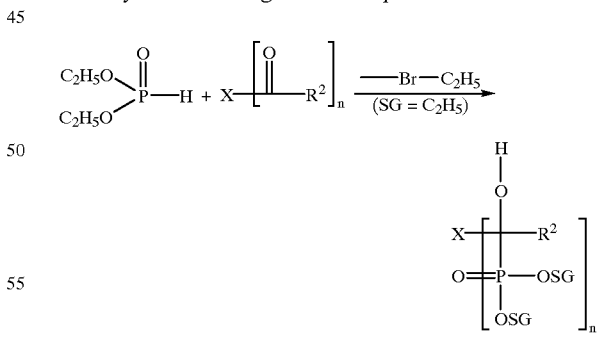

Concrete example:

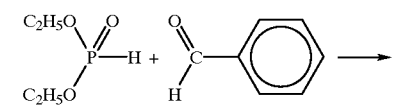

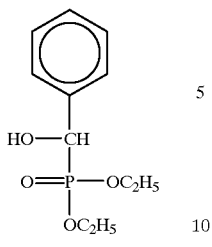
Examples of the acrylphosphonic acids according to the invention of formula (I) are inter alia:
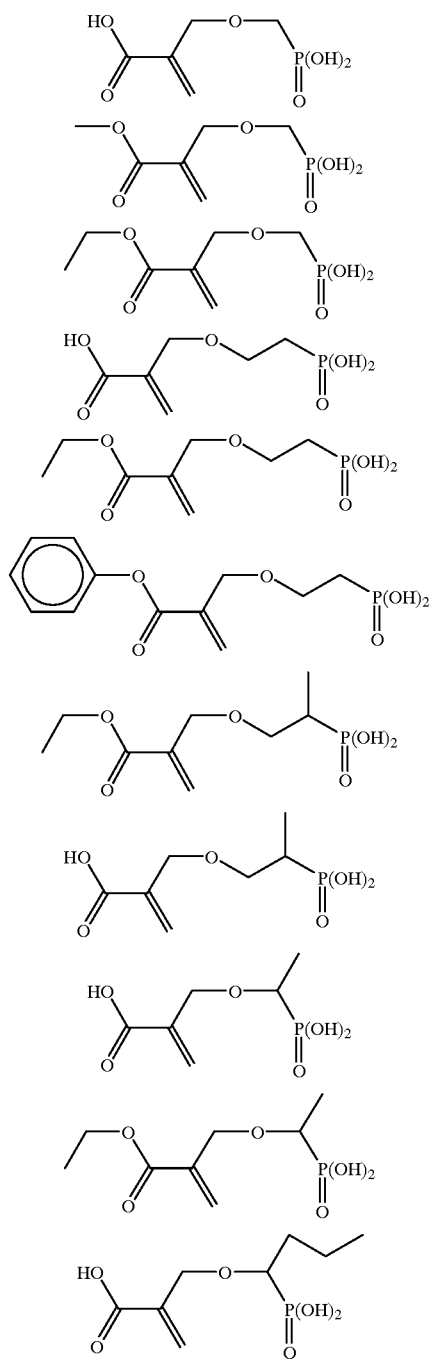
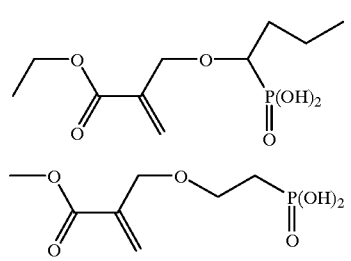
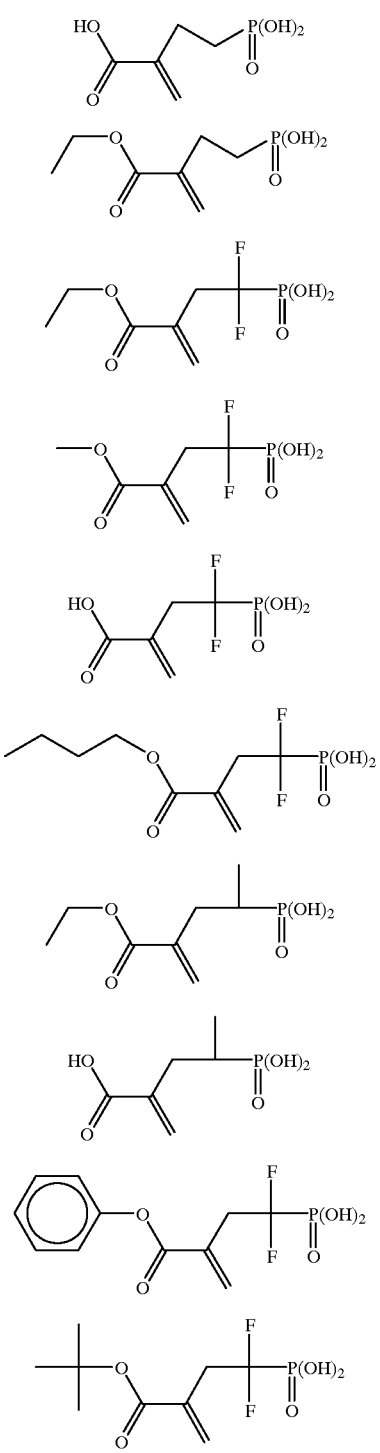

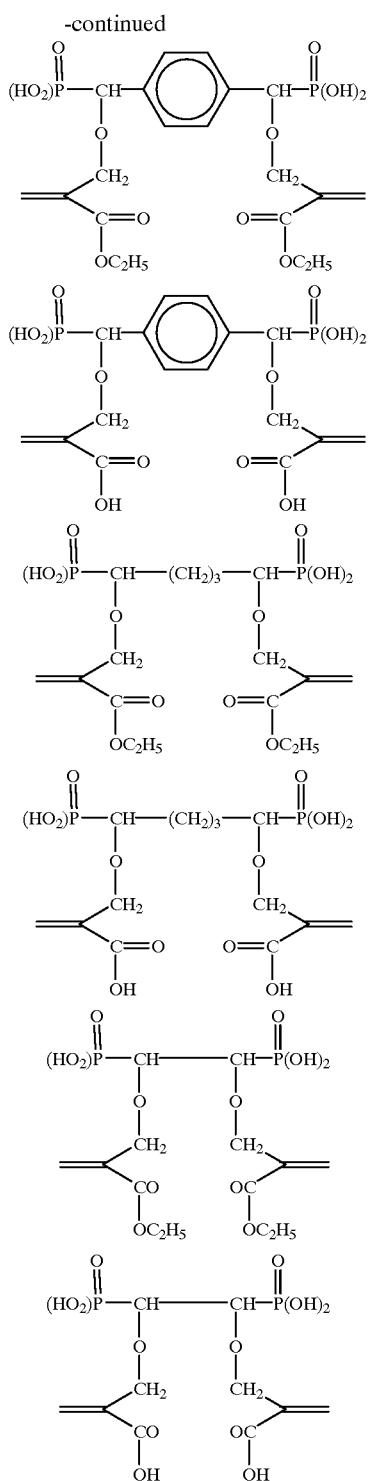

Due to the presence of polymerizable groups the acrylphosphonic acids according to the invention are suitable as starting materials for the preparation of polymers and copolymers. They can be homopolymerized using the known methods of radical polymerization or copolymerized e.g. with suitable comonomers.

In order to carry out the polymerization, the known radical initiators (cf. Encyclopedia of Polymer Science and Engineering, Vol. 13, Wiley-Interscience Publisher, New York 1988, 754 et seq.) can be used. Suitable in particular are azo compounds, such as azobis(isobutyronitrile) (AIBN) or azobis(4-cyanovaleric acid), or peroxides, such as dibenzoyl peroxide, dilauroyl peroxide, tert-butyl peroctoate, tert-butyl perbenzoate or di-(tert-butyl)peroxide.

Benzpinacol and 2,2'-dialkylbenzpinacols are also suitable as initiators for the hot curing.

Furthermore, photoinitiators (cf J. P. Fouassier, J. F. Rabek (publisher), Radiation Curing in Polymer Science and Technology, Vol. II, Elsevier Applied Science, London and New York 1993) can also be used for polymerization with UV light or visible-wavelength light, such as benzoin ethers, dialkylbenzil ketals, dialkoxyacetophenones, acyl phosphine oxides, α-diketones, such as 9,10-phenanthrenequinone, diacetyl, furil, anisil, 4,4'-dichlorobenzil and 4,4'-dialkoxybenzil, and camphor quinone.

The acrylphosphonic acids can be used in particular as a components of adhesives, of cements, of composites and shaped bodies and preferably of dental materials. It is possible that they are present in at least partially polymerized form. Other components with which the acrylphosphonic acids can be combined are mentioned below.

The acrylphosphonic acids according to the invention can be polymerized alone or mixed with conventional radically polymerizable comonomers, in particular with difunctional crosslinking monomers. Suitable for the preparation of adhesives or dental materials are above all crosslinking bi- or polyfunctional acrylates or methacrylates, such as bisphenol-A-di(meth)acrylate, the addition product, called bis-GMA, of methacrylic acid and bisphenol-A-diglycidyl ether; the addition product, called UDMA, of hydroxyethyl methacrylate and 2,2,4-trimethylhexamethylene diisocyanate; di-, tri- or tetraethylene glycol di(meth)acrylate; decanediol di(meth)acrylate; trimethylolpropane tri(meth)acrylate and pentaerythritol tetra(meth)acrylate. The compounds butanediol di(meth)acrylate, 1,10-decanediol di(meth)acrylate and 1,12-dodecanediol di(meth)acrylate, which can be obtained by esterification of (meth)acrylic acid with the corresponding diols, are also suitable.

Moreover, the acrylphosphonic acids according to the invention or mixtures thereof with other radically polymerizable comonomers can be filled with organic or inorganic particles or fibres in order to improve the mechanical properties. Preferred inorganic particulate fillers are amorphous spherical materials based on mixed oxides of $SiO_2$, $ZrO_2$ and/or $TiO_2$, microfine fillers such as pyrogenic silica or precipitated silica, and macro- or mini-fillers, such as quartz powder, glass ceramic powder or glass powder having an average particle size of 0.01 to 5 $\mu$m. Finally, X-ray-opaque fillers, such as ytterbium trifluoride, or glass fibres, polyamide fibres or carbon fibres can also be used.

If necessary, further components can be added to the acrylphosphonic acids, above all solvents, such as water, ethyl acetate, acetone, ethanol or mixtures thereof, and stabilizers, UV absorbers, dyes, pigments or lubricants.

The acrylphosphonic acids according to the invention are suitable in particular as a component of dental materials, such as fixing cements and filling composites and above all dental adhesives.

Such materials are characterized by very good adhesion to different substrates, such as tooth dentine and metallic substrates, which can be attributed to the acrylphosphonic acids used. It is assumed that the acrylphosphonic acids form ionic and/or complex compounds with the calcium ions of the tooth dentine or with the metal ions of metallic substrates. These result in a greater adhesion than would be possible on the basis of simple dipole-dipole or van der Waals' interaction.

The surprisingly high hydrolytic stability of the acrylphosphonic acids also endows the materials according to the invention with a very good hydrolytic stability. This is true both for the unpolymerized and the polymerized material. A high hydrolytic stability is naturally of particular importance to those materials which are permanently exposed to aqueous media, as is precisely the case with dental materials which are planned to reside in the oral cavity for a relatively long time.

Preferred dental materials according to the invention contain the following components (a), (b), (c), (d) and/or (e):

(a) 1 to 99 wt. %, preferably 10 to 80 wt. % and particularly preferably 20 to 70 wt. % acrylphosphonic acids according to the invention, (b) 0.01 to 5 wt. % and preferably 0.1 to 2.0 wt. % radical initiator, (c) 0 to 80 wt. %, preferably 0 to 60 wt. % and particularly preferably 0 to 50 wt. % radically polymerizable comonomers, (d) 0 to 95 wt. %, preferably 0 to 80 wt. % and particularly preferably 0 to 70 wt. % solvent, (e) 0 to 90 wt. %, particularly preferably, depending on the application, 0 to 20 wt. % (adhesive), 20 to 60 wt. % (cement) and 60 to 85 wt. % (filling composite) filler.

The invention is explained in more detail below with reference to examples.

EXAMPLES

Example 1

1st stage: 2-[3-(diethoxyphosphoryl)-2-oxa-propyl]-acrylic acid ethyl ester (1)

7.45 g (50 mmol) α-chloromethylacrylic acid ethyl ester were added at room temperature with stirring to a solution of 8.4 g (50 mmol) hydroxymethylphosphonic acid diethyl ester, which is easily obtainable by reacting diethyl phosphite with paraformaldehyde, 5.05 g (50 mmol) triethylamine (TEA) and 0.01 g phenothiazine (stabilizer) in 40 ml absolute tetrahydrofuran (THF). After 30 minutes' stirring at room temperature, the mixture was heated under reflux for 16 hours. After cooling to room temperature, the formed precipitate of triethylammonium chloride was filtered off. The filtrate was diluted with 150 ml water, set to a pH value of ca. 5 to 7 with 2N hydrochloric acid and extracted repeatedly with diethyl ether. After drying over anhydrous $Na_2SO_4$, the extract was concentrated in a rotary evaporator, dried under a medium vacuum and finally distilled by fractionation. 10.8 g [b.p.: 120–125° C. (0.007 mbar)] of a colourless liquid were obtained (77% yield).

Elemental analysis:

$C_{11}H_{21}O_6P$ Calc.: C 47.14; H, 7.55. (280.26) Found: C 47.58; H, 7.87.

IR (KBr, $cm^{-1}$): 780 (w), 818 (w), 877 (w), 967 (s), 1029 (s,sh), 1112 (s), 1176 (m), 1261 (s), 1306 (m), 1392 (m,sh), 1446 (w), 1719 (s), 2908 (w) and 2984 (m).

$^1$H-NMR (300 MHz, $CDCl_3$, ppm): 1.29–1.42 (m, 9H, $CH_3$), 3.80 (d, 2H, $CH_2$—P), 4.10–4.26 (m, 6H, $CH_2$—$CH_3$), 4.34 (s, 2H,$CH_2$—C=$CH_2$), 5.90 and 6.33 (s, 2×1H, C=$CH_2$).

$^{13}$C-NMR (75 MHz, $CDCl_3$, ppm): 14.20 and 16.47 ($CH_3$↓), 60.78, 62.50, 63.68, 65.89 and 71.38 (all $CH_2$↑), 126.66 ($CH_2$=C↓), 136.64 ($CH_2$=C(-)) and 165.51 (C=O (-)).

$^{31}$P-NMR (121.5 MHz, $CDCl_3$, ppm): 43.0.

2nd stage: 2-[3-(dihydroxyphosphoryl)-oxa-propyl]-acrylic acid ethyl ester (2)

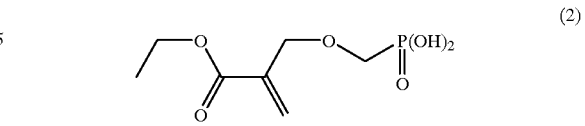

(2)

16.8 g (110 mmol) trimethylsilyl bromide were added dropwise to a solution of 14.0 g (50 mmol) of compound (1) and 0.01 g hydroquinone monomethyl ether (MEHQ, stabilizer) in 30 ml absolute methylene chloride, and the mixture was stirred for 90 minutes under reflux. The mixture was then concentrated in a rotary evaporator, and the obtained residue was stirred for 2 hours after being taken up in 50 ml methanol. After treating the slightly reddish solution with activated charcoal, the solution was concentrated in vacuo and then dried under a medium vacuum until the weight was constant. 9.1 g (81% yield) of a viscous oil remained which had a purity of 98% determined by means of HPLC.

Elemental analysis:

$C_7H_{13}O_6P$ Calc.: C 37.51; H, 5.85. (224.15) Found: C 37.26; H, 6.87

IR (KBr, $cm^{-1}$): 684 (w), 778 (w), 820 (m), 861 (m), 970 (s), 1020 (s), 1112 (s), 1182 (s,sh), 1309 (s,sh), 1405 (m,sh), 1466 (m,sh), 1632 (m), 1713 (s), 2324 (b) and 2600–3500 (b).

$^1$H-NMR (300 MHz, acetone-$d_6$ ppm): 0.32 (ca. 1% silyl compound), 1.28 (t, 3H, $CH_3$), 3.86 (d, 2H, $PCH_2$), 4.20 (q, 2H, $CH_2CH_3$), 4.33 (s, 2H, $CH_2$C=C), 5.96 and 6.30 (s, 2×1H, C=$CH_2$) and 11.38 (s, b, 2H, OH).

$^{13}$C-NMR (75 MHz, acetone-$d_6$, ppm): 14.2 ($CH_3$↓), 61.25 ($CH_2CH_3$↑), 64.75 and 66.9 (d, $CH_2$P↑), 71.35 ($CH_2$C=C↑), 126.15 (C=$CH_2$↑), 137.6 (C=$CH_2$(-)) and 165.75 (C=O).

$^{31}$P-NMR (121.5 MHz, acetone-$d_6$, ppm): 47.0.

Example 2

1st stage: 2-[4-dimethoxyphosphoryl)-2-oxa-butyl]-acrylic acid ethyl ester (3)

7.45 g (50 mmol) α-chloromethylacrylic acid ethyl ester were added at room temperature with stirring to a solution of 7.7 g (50 mmol) hydroxyethylphosphonic acid dimethyl ester, 5.05 g (50 mmol) TEA and 0.01 g phenothiazine in 40 ml absolute THF. The process was then continued analogously to Example 1 (1st stage). The fractional distillation produced 2.1 g [b.p. 115–120° C. (0.005 mbar)] of a colourless liquid (16% yield).

Elemental analysis:

$C_{10}H_{19}O_6P$ Calc.: C 45.11; H, 7.19. (266.23) Found: C 45.45; H, 7.26

IR (KBr, $cm^{-1}$): 645 (w), 732 (m), 820 (s), 954 (m), 1032 (s,b), 1105 (s), 1179 (s), 1267 (s), 1306 (s), 1375 (m,sh), 1464 (m,sh), 1640 (m), 1715 (s), 2234 (w), 2956 (m,sh) and 3472 (w,b).

$^1$H-NMR (300 MHz, $CDCl_3$, ppm): 1.31 (t, 3H, $CH_3CH_2$), 2.10–2.21 (m, 2H, $CH_2$P), 3.71–3.83 (m, 8H, 2×$CH_3$O+$CH_2CH_2$O), 4.18–4.28 (m, 4H, $CH_3CH_2$O+$CH_2$C=), 5.89 and 6.29 (s, 2×1H, C=$CH_2$).

$^{13}$C-NMR (75 MHz, $CDCl_3$, ppm): 14.2 ($CH_3CH_2$↓), 24.0 and 27.0 ($CH_2$P↑), 52.3 ($CH_3$O), 60.95 ($CH_3CH_2$↑), 64.6 ($CH_2CH_2$O↑), 69.0 (O$CH_2$C=C↑), 126.0 (C=$CH_2$↑), 137.4 (C=$CH_2$(-)) and 165.6 (C=O(-)).

$^{31}$PNMR (121.5 MHz, $CDCl_3$, ppm): 62.0.

2nd stage: 2-[4-dihydroxyphosphoryl)-2-oxa-butyl]-acrylic acid ethyl ester (4)

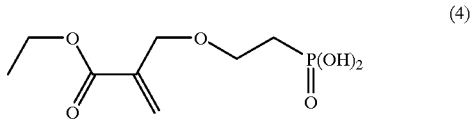

(4)

Analogously to Example 1 (2nd stage), 7.7 g (50 mmol) trimethylsilyl bromide were added dropwise to a solution of 6.1 g (23 mmol) of compound (3) and 0.01 g MEHQ in 20 ml absolute methylene chloride. The mixture was stirred for a further 90 minutes under reflux, then concentrated, and the residue was reacted with 30 ml methanol and treated in accordance with Example 1 (2nd stage). After drying under a medium vacuum until the weight was constant, 4.3 g (79% yield) of a viscous oil was obtained as product.

Elemental analysis:
$C_8H_{15}O_6P$ Calc.: C 40.34; H, 6.35. (238.18) Found: C 40.86; H, 6.52

IR (KBr, cm$^{-1}$): 718 (w), 820 (w), 1024 (s,sh), 1103 (s), 1178 (s,sh), 1273 (m,sh), 1307 (m), 1376 (m,sh), 1466 (w,sh), 1637 (m), 1717 (s), 2323 (b) and 2800–3300 (m,b).

$^1$H-NMR (300 MHz, acetone-d$_6$, ppm): 1.28 (t, 3H, CH$_3$), 2.07–2.24 (m, 2H, CH$_2$P), 3.72–3.84 (m, 2H, CH$_2$CH$_2$O), 4.15–4.25 (m, 4H, CH$_3$CH$_2$O+CH$_2$C=C), 5.93 and 6.25 (s, 2×1H, CH$_2$=) and 9.80 (s, 2H, OH).

$^{13}$C-NMR (75 MHz, acetone-d$_6$, ppm: 13.0 (CH$_3$), 27.8 and 30.3 (d, CH$_2$P), 61.4 (CH$_2$CH$_3$), 65.58 (CH$_2$CH$_2$O), 71.6 (CH$_2$C=CH$_2$), 125.7 (CH$_2$C=CH$_2$), 138.5 (CH$_2$C=CH$_2$) and 166.1 (C=O).

$^{31}$P-NMR (121.5 MHz, CDCl$_3$, ppm): 60.0.

Example 3

1st stage: 1,4-bis[1-(diethoxyphosphoryl)-1-hydroxymethyl]-benzene (5)

1.1 g (0.01 mol) DABCO were added at ca. 15° C. with stirring to a solution of 13.4 g (0.1 mol) terephthalic aldehyde and 29.0 g (0.2 mol) diethyl phosphite in 50 ml absolute acetonitrile. After further stirring over night, the formed precipitate was removed by suction, washed in each case with some acetonitrile and petroleum ether and dried until the weight was constant. 30.7 g (75% yield) of a white solid (m.p.: 195–200° C.) were obtained.

Elemental analysis:
$C_{16}H_{28}O_8P_2$ Calc.: C 46.83; H, 6.68. (410.34) Found: C 46.79; H, 6.43

IR (KBr, cm$^{-1}$): 445 (w), 494 (w), 575 (s), 658 (w), 758 (m), 791 (w), 831 (w), 861 (w), 975 (s), 1022 (s), 1056 (s), 1205 (s), 1230 (s), 1392 (m), 1445 (w), 1478 (w), 1509 (w), 1702 (w), 2911 (w), 2988 (m) and 3263 (s,b).

$^1$H-NMR (300 MHz, DMSO-d$_6$, ppm): 1.12–1.18 (m, 12H, CH$_3$), 3.82–3.98 (m, 8H, CH$_2$), 4.92 (d, 2H, CH—P), 6.20 (s, 2H, OH, H/D exchange) and 7.38 (s, 4H, CH-arom.).

$^{13}$C-NMR (100 MHz, DMSO-d$_6$, ppm): 16.13 and 16.23 (s, CH$_3$), 61.68 and 62.08 (s, CH$_2$), 68.31 and 69.93 (d, CH—P), 126.68 (s, CH-arom.) and 137.54 (s, quart. arom. C).

$^{31}$P-NMR (162 MHz, DMSO-d$_6$, ppm): 21.9.

2nd stage: 1,4-bis[1-(diethoxyphosphoryl)-1-[(2-methylen-3-yl-propanoic acid ethyl ester)-oxy]methyl]-benzene (6)

8.9 g (60 mmol) α-chloromethylacrylic acid ethyl ester were added at room temperature and with stirring to a solution of 12.3 g (0.03 mol) of compound (5), 6.05 g (60 mmol) TEA and 0.02 g phenothiazine in 100 ml absolute THF. After 30 minutes' stirring at room temperature, the mixture was heated under reflux for 16 hours. After cooling to room temperature, the formed precipitate as filtered off, washed once with diethyl ether and twice with water. After drying of the residue at 60° C. under a medium vacuum, 9.7 g (51% yield) of a colourless resin were obtained.

Elemental analysis:
$C_{28}H_{44}O_{12}P_2$ Calc.: C 52.98; H, 6.99. (634.60) Found: C 52.98; H, 7.08

IR (KBr, cm$^{-1}$): 580 (s), 751 (m), 795 (m), 859 (w), 967 (s), 1028 (s), 1055 (s), 1095 (s), 1177 (s), 1257 (s), 1308 (s,sh), 1391 (s,sh), 1445 (m,sh), 1508 (w), 1636 (m), 1716 (s), 2930 (m,sh) and 2982 (s).

$^1$N-NMR (400 MHz, acetone-d$_6$, ppm): 1.10–1.22 (m, 18H, CH$_3$), 3.95–4.01 (m, 8H, POCH$_2$CH$_3$), 4.10–4.16 (m, 8H, COCH$_2$), 4.95 (d, 2H, CH), 5.97 and 6.27 (s, 2×2H, CH$_2$=) and 7.43 (s, 4H, CH-arom.).

$^{13}$C-NMR (100 MHz, acetone-d$_6$, ppm): 14.16 (CH$_3$-methacrylate), 16.37 (CH$_3$-phosphonate) 60.73 (OCH$_2$CH$_3$-methacrylate), 62.9 and 63.2 (d, OCH$_2$CH$_3$-phosphonate), 68.70 and 68.83 (d, CH—P), 126.82 and 128.54 (CH$_2$= and CH-arom.), 134.97 and 136.75 (CH$_2$=C and C-arom.) and 165.37 (C=O).

$^{31}$P-NMR (121.5 MHz, DMSO-d$_6$, ppm): 18.6.

3rd stage: 1,4-bis[11-(dihydroxophosphoryl)-1-[(2-methylen-3-yl-propanoic acid ethyl ester)oxylmethyl]-benzene (7)

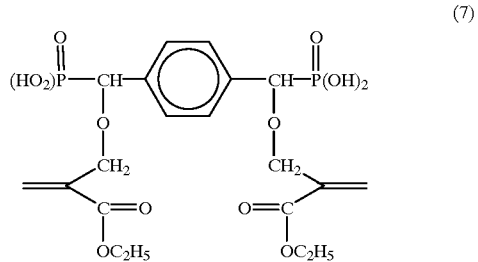

(7)

8.6 g (56 mmol) trimethylsilyl bromide were added dropwise to a solution of 7.8 g (12.3 mmol) of compound (6) and 0.01 g MEHQ in 20 ml absolute methylene chloride, and the mixture obtained was stirred under reflux for 75 minutes. The mixture was then concentrated in a rotary evaporator. After 20 ml methanol had been added to the residue, it was stirred over night and concentrated again in vacuo. The formed light-yellow powder was taken up in 100 ml of a saturated NaHCO$_3$ solution and washed twice with in each case 50 ml methylene chloride. The solution was then stirred up with activated charcoal and filtered. The filtrate was set to pH=1 with concentrated hydrochloric acid, treated with 2 g NaCl and 50 ml water and then shaken out three times with in each case 150 ml methylene chloride. The combined extracts were dried over Na$_2$SO$_4$ and concentrated until dry in a rotary evaporator. The residue was dried under a medium vacuum until the weight was constant. 4.3 g (66% yield) of a weakly yellowish crystalline product remained.

Elemental analysis:
$C_{20}H_{28}O_{12}P_2$ Calc.: C 45.99; H, 5.45. (522.39) Found: C 44.96; H, 4.93

IR (KBr, cm ): 412 (m), 569 (s), 646 (w), 815 (m), 941 (s), 1035 (s), 1093 (s), 1176 (s), 1285 (sh), 1320 (sh), 1390 (sh), 1406 (m), 1460 (w), 1509 (m), 1636 (m), 1717 (s), 2987 (s) and 3440 (s,b).

$^1$H-NMR (300 MHz, DMSO-d$_6$/ CDCl$_3$, ppm): 1.17 (t, 6H, CH$_3$), 4.12–4.33 (m, 8H, CH$_2$), 4.50–4.55 (d, 2H, CH), 6.08 and 6.27 (s, 2×1H, =CH$_2$), 7.36 (s, 4H, CH-arom.) and 9–10 (4H, b, OH).

$^{13}$C-NMR (100 MHz, DMSO-d$_6$/CDCl$_3$, ppm) 14.01 (CH$_3$), 60.37 (OCH$_2$CH$_3$), 68.10 and 68.23 (d, CH—P), 125.87 and 127.49 (CH$_2$= and CH-arom.), 135.64 and 136.85 (CH$_2$=C and C-arom.) and 165.34 (C=O).

$^{31}$P-NMR (121.5 MHz, DMSO-d$_6$, ppm): 15.1.

Example 4

1st stage: [(dimethoxyphosphoryl)-[(2-methylen-3-yl-propanoic acid ethyl ester)oxy]-methyl]benzene (8)

14.9 g (0.1 mol) α-chloromethylacrylic acid ethyl ester were added at room temperature with stirring to a solution of 21.6 g (0.1 mol) [(dimethoxyphosphoryl)-1-hydroxymethyl]benzene, which can be obtained by reacting dimethyl phosphite with benzaldehyde (F. Texier-Boullet, A. Foucaud, Synthesis 1982, 916), 10.1 g (0.1 mol) TEA and 0.02 g phenothiazine in 200 ml absolute THF. After 30 minutes' stirring at room temperature, the mixture was heated for 16 hours under reflux. After cooling to room temperature, the formed precipitate was filtered off, and this was washed once with diethyl ether. The washing ether and the filtrate were diluted with 400 ml water, and the mixture obtained was extracted three times with in each case 100 ml ether. The combined organic extracts were washed with 100 ml saturated NaCl solution, dried over Na$_2$SO$_4$ and concentrated in a rotary evaporator. The remaining oily residue was then destined under a high vacuum. 15.9 g (49% yield) of a colourless liquid [b.p.: 153–155° C. (10 mbar)] were obtained.

Elemental analysis:
C$_{15}$H$_{21}$O$_6$P Calc.: C 54.88; H, 6.45. (328.30) Found: C 54.10; H, 6.24

IR (KBr, cm$^{-1}$): 465 (s,b), 701 (m), 771 (w), 832 (m), 1031 (s,sh), 1095 (s), 1181 (s), 1262 (s), 1309 (m), 1401 (w), 1453 (m), 1637 (w), 1718 (s), 2854 (w) and 2956 (m).

$^1$N-NMR (300 MHz, CDCl$_3$, ppm): 1.29 (t, 3H, CH$_3$CH$_2$), 3.65–3.73 (dd, 6H, POCH$_3$), 4.14–4.33 (m, 4H, CH$_2$), 4.78 (d, 1H, CH), 5.97 and 6.34 (s, 2×1H, CH$_2$=) and 7.34–7.47 (m, 5H, CH-arom.).

$^{13}$C-NMR (100 MHz, CDCl$_3$, ppm) : 14.45 (s, CH$_3$-methacrylate↑); 54.17 (d, CH$_3$—OP↑); 61.07 (OCH$_2$CH$_3$-methacrylate↓); 69.88 (s, OCH$_2$C=CH$_2$↓); 77.34 and 79.31 (d, CH—P↑); 126.87 (s, CH$_2$=↓); 128.32 and 128.86 (s, CH-arom.↑); 134.97 and 136.75 (CH$_2$=C and C-arom.(–)); 165.37 (C=O(–)).

$^{31}$P-NMR (121.5 MHz, CDCl$_3$, ppm): 21.3 (s).

2nd stage: 1-(dihydroxyphosphoryl)-1-[(2-methylen-3-yl-propionic acid ethyl ester)-oxy]methyl]-benzene (9)

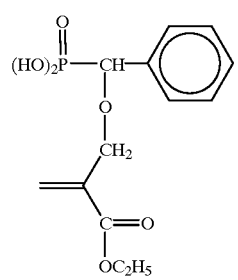

(9)

17.2 g (0.1 mol) trimethylsilyl bromide were added dropwise to a solution of 14.4 g (44 mmol) of compound (8) and 0.01 g MEHQ in 40 ml absolute methylene chloride, and the mixture obtained was stirred under reflux for 75 minutes. The mixture was then concentrated in a rotary evaporator, and the residue was reacted with 40 ml methanol. The mixture was stirred for 4 hours and concentrated in vacuo. The formed resin was taken up in 200 ml of a saturated NaHCO$_3$ solution and washed twice with 100 ml methylene..chloride. The solution was stirred up with activated charcoal and filtered. The filtrate was then set to pH=1 with concentrated hydrochloric acid, treated with 4 g NaCl and 50 ml water and then shaken out three times with in each case 100 ml methylene chloride. The combined extracts were dried over Na$_2$SO$_4$ and concentrated until dry in a rotary evaporator. The residue was dried under a medium vacuum until the weight was constant. 10.0 g (76% yield) of a sticky crystalline product were obtained.

Elemental analysis:
C$_{13}$H$_{17}$O$_6$P Calc.: C 52.00; H, 5.71. (300.25) Found: C 50.47; H, 5.58

IR (KBr, cm$^{-1}$): 698 (s), 739 (w), 805 (w), 819 (w), 970 (s), 1026 (s,sh), 1094 (s,sh), 1178 (s,sh), 1280 (s,sh), 1320 (m), 1340 (m), 1402 (m,sh), 1453 (m,sh), 1490 (m), 1643 (m), 1713 (s), 2321 (m), 2910 (m), 2949 (m) and 2982 (m).

$^1$H-NMR (300 MHz, CDCl$_3$, ppm): 1.22 (t, 3H, CH$_3$), 4.06–4.17 (m, 4H, CH$_2$), 4.50 (d, 2H, CH—P), 5.89 and 6.19 (s, 2×1H, CH$_2$=), 7.18–7.33 (m, 5H, CH-arom.) and 10.79 (s, 2H, OH, H/D exch.).

$^{13}$C-NMR (100 MHz, CDCl$_3$, ppm): 14.08 (CH$_3$); 60.86 (OCH$_2$CH$_3$); 68.49 (CH$_2$OCH); 77.20 and 78.86 (d, CH—P); 127.49–128.25, 135.21, 136.15 (all C-arom.+ CH$_2$=C) and 166.08 (C=O).

$^{31}$P-NMR (121.5 MHz, CDCl$_3$, ppm): 20.1.

Example 5

Radical homopolymerization of acrylphosphonic acid (7)

2.61 g (5.0 mmol) of the acrylphosphonic acid (7) used as monomer and 2.5 mol % azobis(isobutyronitrile), relative to the monomer, were dissolved in 9.0 ml ethanol in a Schlenk vessel. The monomer solution was degassed by being repeatedly frozen under argon and defrosted under a medium vacuum and then polymerized at 65° C. under argon. On account of the difunctional monomer structure, crosslinked and therefore insoluble polymeric acrylphosphonic acid (7) was already deposited after 2 minutes. The monomer conversion was 47.7% after 1 hour. The formed polymer was insoluble.

Example 6

Examination of the hydrolytic stability of the monomeric acrylphosphonic acids 20 wt. % solutions in EtOD/H$_2$O (1:1 parts by volume) were prepared from each of the monomeric acrylphosphonic acids (2) and (7) according to the invention and from monomeric 2-(methacryloyloxy)ethylphosphonic acid (10) as a comparative example and were stored at 25 and 37° C. To determine the hydrolytic stability, an $^1$H-NMR spectrum was recorded after various times and was analysed for the formation of possible cleavage products.

It was shown that no hydrolytic cleavage of the polymerizable group had taken place in the case of the acrylphosphonic acids (2) and (7) according to the invention even after 3 months, whereas in the case of the conventional acrylphosphonic acid (10) the cleavage of the ethylphosphonic acid group began after just a few hours at 25° C. and was detectable by the presence of 2-hydroxyethylphosphonic acid as a cleavage product. This suggests a hydrolytic cleavage according to the following formula.

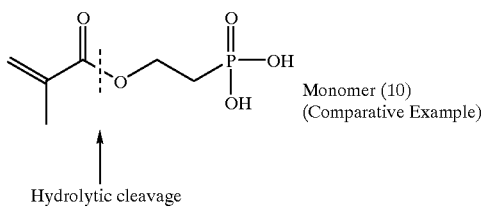

Monomer (10)
(Comparative Example)

Hydrolytic cleavage

Example 7
Examination of the adhesion to metal of the acrylphosphonic acids

Wiron 88 (Thyssen-Bego), an Ni—Cr—Mo dental alloy customary in the trade, was sandblasted and cleaned with superheated steam. A primer consisting of 10.0 wt. % of the acrylphosphonic acid (7), 45.0 wt. % water, 44.7 wt. % ethanol and 0.3 wt. % camphor quinone was then brushed on in a thin layer, and Variolink (Vivadent Ets., Liechtenstein), a commercial light-curing adhesive for filling composites, was applied to it and exposed to light. A dividible Teflon mould (d=4 mm, h=6 mm) was then fixed with a securing means to the metal surface, and a light-curing filling composite, namely Tetric (Vivadent Ets., Liechtenstein) was polymerized in layers onto the metal surface in a volume predetermined by the Teflon mould and on an adhesion surface thereby determined. The shear strength values were determined after 24 hours' storage in water at 37° C. according to ISO-TR 11 405. The adhesive strength ascertained in the shear test gave an excellent value of 11.6±2.0 MPa.

We claim:
1. Hydrolysis-stable and polymerizable acrylphosphonic acids of the general formula (I), stereoisomers thereof and mixtures of these

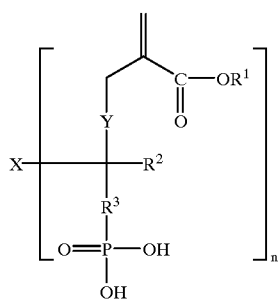

(I)

where $R^1$, $R^2$, $R^3$, X, Y and n, unless stated otherwise, independently of one another have the following meanings:
$R^1$=hydrogen, $C_1$ to $C_{10}$ alkyl or $C_6$ to $C_{10}$ aryl,
$R^2$=hydrogen, $C_1$ to $C_5$ alkyl or phenyl,
$R^3$=$C_1$ to $C_8$ alkylene, phenylene or is absent,
Y=oxygen, sulphur, $C_1$ to $C_8$ alkylene or is absent,
n=1 or 2,
and with the proviso that
(a) for n=1
X=hydrogen, $C_1$ to $C_5$ alkyl or $C_6$ to $C_{12}$ aryl, and
(b) for n=2
X=$C_1$ to $C_{10}$ alkylene, $C_6$ to $C_{10}$ arylene, $C_7$ to $C_{20}$ arylenalkylene or is absent,
and in which the individual alkyl, aryl, alkylene, arylene, phenyl, phenylene and arylenalkylene radicals can bear one or more substituents.

2. Acrylphosphonic acids according to claim 1, wherein the variables of the formula (I), unless otherwise stated, independently of one another have the following meanings:
$R^1$=hydrogen, $C_1$ to $C_5$ alkyl or phenyl,
$R^2$=hydrogen, or $C_1$ to $C_3$ alkyl,
$R^3$=$C_1$ to $C_3$ alkylene, phenylene or is absent,
Y=oxygen, $C_1$ to $C_3$ alkylene or is absent,
n=1 or 2,
and with the proviso that
(a) for n=1
X=hydrogen, $C_1$ to $C_3$ alkyl or phenyl,
and
(b) for n=2
X=$C_1$ to $C_6$ alkylene, phenylene or is absent.

3. A process for the preparation of acrylphosphinic acids of the general formula (I), stereoisomers thereof and mixtures of these

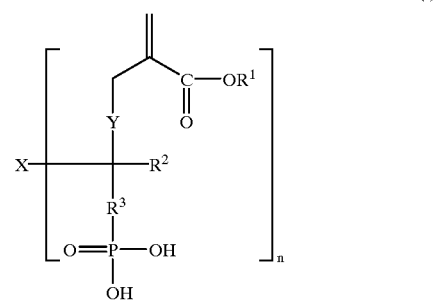

(I)

where $R^1$, $R^2$, $R^3$, X, Y and n, unless stated otherwise, independently of one another have the following meanings:;
$R^1$=hydrogen, $C_1$ to $C_{10}$ alkyl or $C_6$ to $C_{10}$ aryl,
$R^2$=hydrogen, $C_1$ to $C_5$ alkyl or phenyl,
$R^3$=$C_1$ to $C_8$ alkylene, phenylene or is absent,
Y=oxygen, sulphur, $C_1$ to $C_8$ alkylene or is absent,
n=1 or 2,
and with the proviso that
(a) for n=1
X=hydrogen, $C_1$ to $C_5$ alkyl or $C_6$ to $C_{12}$ aryl,
and
(b) for n=2
X=$C_1$ to $C_{10}$ alkylene, $C_6$ to $C_{10}$ arylene, $C_2$ to $C_{20}$ arylenalkylene or is absent,
and in which the individual alkyl, aryl, alkylene, arylene, phenyl, phenylene and arylenalkylene radicals can bear one or more substituents,
wherein α-halomethylacrylic acid esters of the general formula (II)

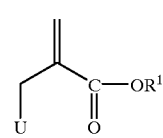

(II)

are reacted with protected mono- or difunctional phosphonic acid esters of the general formula (III)

(III)

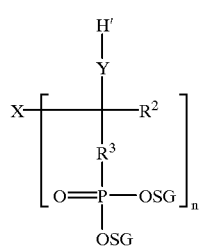

and the protective groups are cleaved off, with

U=halogen,

SG=protective group.

4. A composition comprising the acrylphosphonic acids according to claim 1 wherein the composition is selected from the group consisting of an adhesive, a polymer, a composite, a cement, a shaped body, and a dental material.

5. A dental material comprising an acrylphosphinic acid of the general formula (I), stereoisomers thereof and mixtures of these

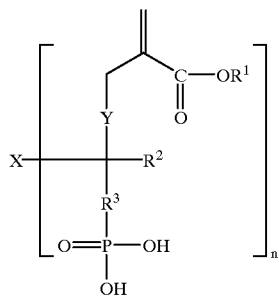

(I)

where $R^1$, $R^2$, $R^3$, X, Y and n, unless stated otherwise, independently of one another have the following meanings:

$R^1$=hydrogen, $C_1$ to $C_{10}$ alkyl or $C_6$ to $C_{10}$ aryl, $R^2$=hydrogen, fluorine, $C_1$ to $C_5$ alkyl or phenyl, $R^3$=$C_1$ to $C_8$ alkylene, phenylene or is absent, Y=oxygen, sulphur, $C_1$ to $C_8$ alkylene or is absent, n=1 or 2, and with the proviso that (a) for n=1

X=hydrogen, fluoride, $C_1$ to $C_5$ alkyl or $C_6$ to $C_{12}$ aryl, and

X=$C_1$ to $C_{10}$ alkylene, $C_6$ to $C_{10}$ arylene, $C_7$ to $C_{20}$ arylenalkylene or is absent, and in which individual alkyl, aryl, alkylene, arylene, phenyl, phenylene and arylenalkylene radicals can bear one or more substituents wherein the dental material is a dental adhesive, a fixing cement or a filling composite.

6. The composition according to claim 4, wherein the acrylphosphonic acids are present in at least partially polymerized form.

7. A dental material comprising an acrylphosphinic acid of the general formula (I), stereoisomers thereof and mixtures of these

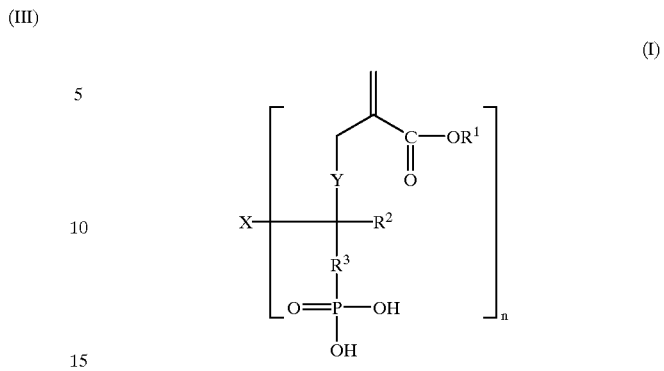

(I)

where $R^1$, $R^2$, $R^3$, X, Y and n, unless stated otherwise, independently of one another have the following meanings:

$R^1$=hydrogen, $C_1$ to $C_{10}$ alkyl or $C_6$ to $C_{10}$ aryl, $R^2$=hydrogen, fluorine, $C_1$ to $C_5$ alkyl or phenyl, $R^3$=$C_1$ to $C_8$ alkylene, phenylene or is absent, Y=oxygen, sulphur, $C_1$ to $C_8$ alkylene or is absent, n=1 or 2, and with the proviso that (a) for n=1

X=hydrogen, fluorine, $C_1$ to $C_5$ alkyl or $C_6$ to $C_{12}$ aryl, and (b) for n=2

X=$C_1$ to $C_{10}$ alkylene, $C_6$ to $C_{10}$ arylene, $C_7$ to $C_{20}$ arylenalkylene or is absent, and in which the individual alkyl, aryl, alkylene, arylene, phenyl, phenylene and arylenalkylene radicals can bear one or more substituents.

8. A dental material comprising an acrylphosphinic acid of the general formula (I), stereoisomers thereof and mixtures of these

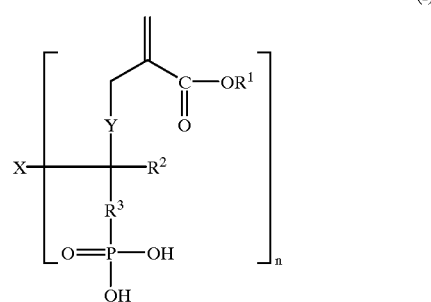

(I)

where $R^1$, $R^2$, $R_3$, X, Y and n, unless stated otherwise, independently of one another have the following meanings:

$R^1$=hydrogen, $C_1$ to $C_{10}$ alkyl or $C_6$ to $C_{10}$ aryl, $R^2$=hydrogen, fluorine, $C_1$ to $C_5$ alkyl or phenyl, $R^3$=$C_1$ to $C_8$ alkylene, phenylene or is absent, Y=oxygen, sulphur, $C_1$ to $C_8$ alkylene or is absent, n=1 or 2, and with the proviso that
(a) for n=1
    X=hydrogen, fluorine, $C_1$ to $C_5$ alkyl or $C_6$ to $C_{12}$ aryl, and
(b) for n=2
    X=$C_1$ to $C_{10}$ alkylene, $C_6$ to $C_{10}$ arylene, phenyl, phenylene and arylenalkylene radicals can bear one or more substituents, wherein the acrylphosphonic acid is in at least partially polymerized form.

9. Polymers and copolymers, which are obtained by polymerization or copolymerization of the acrylphosphonic acids according to claim 1.

* * * * *